United States Patent [19]

Boden

[11] 4,357,316
[45] Nov. 2, 1982

[54] USE OF 1-N-BUTOXY-1-ETHANOL ACETATE FOR AUGMENTING OR ENHANCING THE TASTE OF TOOTHPASTE

[75] Inventor: Richard M. Boden, Monmouth Beach, N.J.

[73] Assignee: International Flavors & Fragrances Inc., New York, N.Y.

[21] Appl. No.: 287,901

[22] Filed: Jul. 29, 1981

Related U.S. Application Data

[60] Division of Ser. No. 217,810, Dec. 18, 1980, Pat. No. 4,296,138, which is a continuation-in-part of Ser. No. 176,111, Aug. 7, 1980, Pat. No. 4,296,137.

[51] Int. Cl.$^3$ ............................................... A61K 7/16
[52] U.S. Cl. ..................................................... 424/49
[58] Field of Search ..................................... 424/49–58

[56] References Cited

U.S. PATENT DOCUMENTS

| | | | |
|---|---|---|---|
| 2,305,621 | 12/1942 | Kremers | 426/534 |
| 3,857,964 | 12/1974 | Yolles et al. | 426/534 X |
| 4,296,137 | 10/1981 | Boden | 426/534 |
| 4,296,138 | 10/1981 | Boden | 426/534 |

OTHER PUBLICATIONS

Shostakovski et al. "Butoxyethyl Acetate" Chemical Abstracts vol. 48#579h (1954).

*Primary Examiner*—Shep K. Rose
*Attorney, Agent, or Firm*—Arthur L. Liberman

[57] ABSTRACT

Described is the use for augmenting or enhancing the taste of toothpaste of 1-n-butoxy-1-ethanol acetate having the structure:

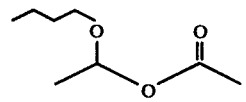

2 Claims, 3 Drawing Figures

GLC PROFILE FOR EXAMPLE I.

NMR SPECTRUM FOR EXAMPLE I.

IR SPECTRUM FOR EXAMPLE I.

USE OF 1-N-BUTOXY-1-ETHANOL ACETATE FOR AUGMENTING OR ENHANCING THE TASTE OF TOOTHPASTE

This application is a division of application for United States Letters Patent Ser. No. 217,810 filed on Dec. 18, 1980, now U.S. Pat. No. 4,296,138 issued on Oct. 20, 1981 which, in turn, is a continuation-in-part of application for United States Letters Patent Ser. No. 176,111 filed on Aug. 7, 1980, now U.S. Pat. No. 4,296,137 issued on Oct. 20, 1981.

BACKGROUND OF THE INVENTION

This invention relates to a novel method of fixing acetaldehyde by means of the formation of 1-n-butoxy-1-ethanol acetate which acts as a generator responding to conditions of use in a food product to yield acetaldehyde. This invention also relates to the use of 1-n-butoxy-1-ethanol acetate having the structure:

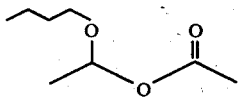

in flavors taken alone or combined in carbohydrates, such as cyclic dextrins to generate acetaldehyde and, at the same time, augment or enhance "grape" and/or wine flavors and/or other fruity flavors such as orange and apple flavors or similarly fruit flavored beverages.

It is well known that acetaldehyde occurs in a wide variety of fresh and prepared foodstuffs, such as fruits, meat, dairy products, baked goods and vegetables. Acetaldehyde has been found particularly important in contributing to the flavor impact in "fresh" effect of certain foodstuffs especially of the citrus fruit and red berry types. As such, it is indispensable in compounding artificial flavors where the "fresh" effect is needed, plus, as early as 1921 acetaldehyde has been indicated to be useful in the formulation of a synthetic apple oil, as indicated in U.S. Pat. No. 1,366,541 issued on June 25, 1921 and as indicated in U.S. Pat. No. 1,436,290 on Nov. 21, 1922. In addition, acetaldehyde has been found to be important in contributing to the flavor impact of coffee flavor. Thus, U.S. Pat. No. 1,696,419 issued on Dec. 25, 1928 as well as United Kingdom Pat. No. 260,960 accepted on Feb. 22, 1928 disclose the utility of acetaldehyde in augmenting and enhancing the aroma and taste of coffee. Although it is also well known to fix acetaldehyde in the form of the diethyl acetal as is seen in U.S. Pat. No. 3,140,184, wherein the diethyl acetal of acetaldehyde and a beta-cyclic dextrin complex are added to a dry beverage mix to produce a pleasant tasting beverage having a characteristic flavor and odor of fresh oranges, the optimization of the rate of generation of acetaldehyde aroma in the citrus-tasting beverage has never quite been achieved. Thus, German Offenlegungschrift No. 2,802,821, published on July 27, 1978 corresponding to United States Application for Letters Patent Ser. No. 761,183, filed on Jan. 21, 1977, discloses a number of acetaldehyde precursors including the acetaldehyde precursor having the structure:

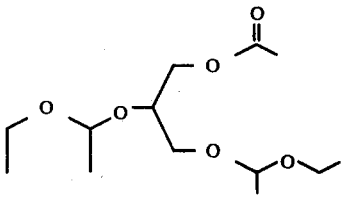

None of the acetaldehyde precursors; either those of German Offenlegungschrift No. 2,802,821, including that having the structure:

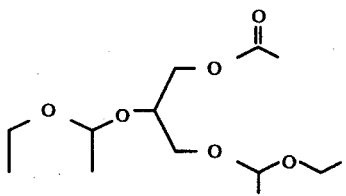

or those of U.S. Pat. No. 3,140,184, including that having the structure:

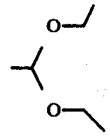

have as advantageous a flavor and aroma impact and have as advantageous a fragrance impact, as 1-n-butoxy-1-ethanol acetate having the structure:

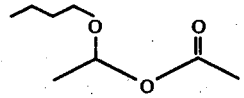

whether it is used as is, or whether it is combined with an absorbing solid such as acyclic dextrin.

THE INVENTION

Figure 1:
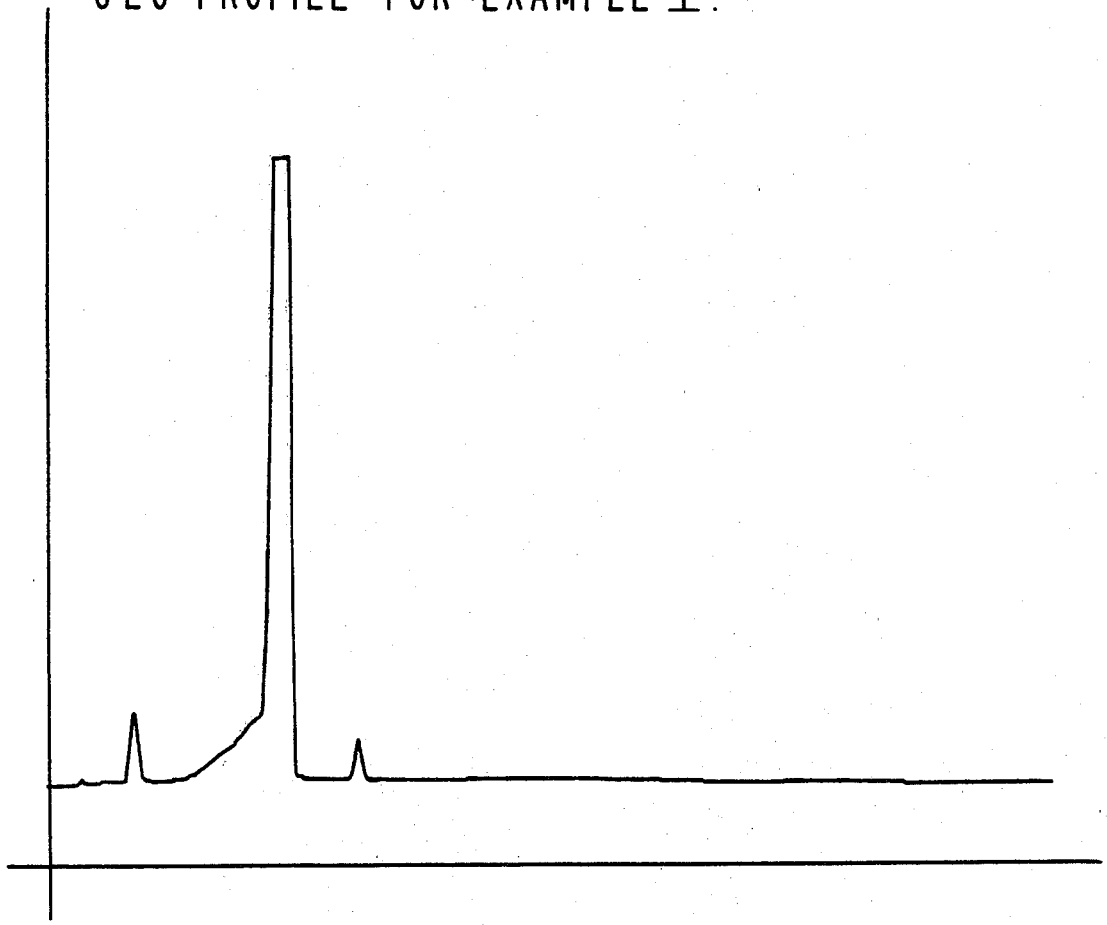
FIG. 1 is the GLC profile for the reaction product of Example I containing 1-n-butoxy-1-ethanol acetate.

It has now been determined that 1-n-butoxy-1-ethanol acetate is capable of imparting a variety of flavors and fragrances to various consumable materials, and is also capable of augmenting or enhancing a variety of flavors and fragrances of various consumable materials.

Briefly, my invention contemplates augmenting or enhancing the flavors and/or fragrances of such consumable materials as perfumes, perfumed articles, colognes, foodstuffs, chewing gums, toothpastes, medicinal products and smoking tobaccos by adding thereto a small but effective amount of 1-n-butoxy-1-ethanol acetate having the structure:

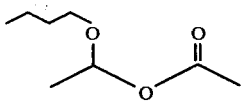

The 1-n-butoxy-1-ethanol acetate of my invention augments or enhances fresh, fruity, grape-like, apple-like, juicy, somewhat acetaldehyde-like, acetic acid-like and ethereal-like aroma and flavor characteristics, insofar as augmenting or enhancing the aroma or taste of foodstuffs, toothpastes, medicinal products and chewing gums.

The 1-n-butoxy-1-ethanol acetate of my invention also augments or enhances the fruity, floral, jasmine, pear-like, banana-like, grape-like and winey aromas of perfumes, perfumed articles and colognes of my invention.

The 1-n-butoxy-1-ethanol acetate of my invention also augments or enhances the sweet, fruity, winey, fresh and berry characteristics of smoking tobacco, both prior to and on smoking, by imparting thereto, a "life" and freshness. The stability advantage of 1-n-butoxy-1-ethanol acetate over acetaldehyde is quite profound, yet its ability to liberate the acetaldehyde nuance is smoking tobacco is unexpected, unobvious and advantageous.

The 1-n-butoxy-1-ethanol acetate of my invention may be prepared according to processes well known in the prior art, for example, according to the reaction:

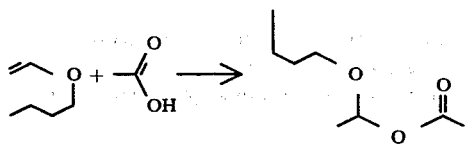

Such a process is more specifically pointed out in the article by Shostakovskii, Gershstein, Bogdanova and Shishov, Akad, Nauk, SSSR, Inst. Org. Khim., Sintezy Org. Soedinenii Sbronik, 2 25–8 (1952) (abstracted in Chem. Abstracts Volume 48, column 579h).

The 1-n-butoxy-1-ethanol acetate of my invention can be obtained in pure form, or in substantially pure form by conventional purification techniques. Thus, the products can be purified and/or isolated by distillation, preparative chromatographic techniques (column chromatography and vapor phase chromatography) and the like. It has been found desirable to purify the 1-n-butoxy-1-ethanol acetate of my invention by fractional distillation in vacuo.

When the 1-n-butoxy-1-ethanol acetate of my invention is used as a food flavor adjuvant, the nature of the co-ingredients included with said 1-n-butoxy-1-ethanol acetate in formulating the product composition will also serve to alter, modify, augment or enhance the organoleptic characteristics of the ultimate foodstuff treated therewith.

As used herein in regard to flavors, the terms "alter", "modify" and augment in their various forms, mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks, and the like.

As used herein, the term "medicinal product" includes both solids and liquids which are ingestible, non-toxic materials which have medicinal value such as cough syrups, cough drops, aspirin and chewable medicinal tablets.

The term "chewing gum" is intended to mean a composition which comprises a substantially water insoluble, chewable plastic gum base such as chicle, or substitutes therefor, including jelutong, guttakay rubber or certain cosmetible natural or synthetic resins or waxes. Incorporated with the gum base in admixture therewith may be plasticizers or softening agents, e.g., glycerine, and a flavoring composition which incorporates the 1-n-butoxy-1-ethanol acetate of my invention, and in addition, sweetening agents which may be sugars, including sucrose or dextrose and/or artificial sweeteners such as cyclamates or saccharin. Other optional ingredients may also be present.

Substance suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxy anisole), butylated hydroxytoluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g. agar agar, carrageenan; cellulose and cellulose derivatives such as, carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like, firming agents such as aluminum sodium sulfate, calcium chloride and calcium gluconate; texturizers, anticaking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alphamethylbutyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanol, crotonal, diacetyl, 2-methylbutanol, beta-beta-dimethyl acrolein, methyl n-amyl ketone, n-hexanal, 2-hexenal, isopentenal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, beta-damascone, alpha-damascone, beta-damascenone, acetophenone, 2-heptanone, o-hydroxy-acetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal, alcohols such as 1-butanol, benzyl alcohol, 1-borneol, trans-2-buten-1-ol, ethanol, geraniol, 1-hexanol, 2-heptanol, trans-2-hexenol-1, cis-3-hexenol-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpinhydrate, eugenol, linalool, 2-heptanol, acetoin; esters such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate, and terpenyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, alphaphellandrene, betaphellandrene, p-cymene 1-alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as γ-nonalactone; sulfides, e.g., methyl sulfide and other materials such as maltol, and acetals (e.g., 1,1-diethoxyethane, 1,1-dimethyloxyethane and dimethoxymethane), piperine, chavicine, and piperdine.

The specific flavoring adjuvant selected for use may be either solid or liquid depending upon the desired physical form of the ultimate product, i.e., foodstuff, whether simulated or natural, and should, in any event, (i) be organoleptically compatible with the 1-n-butoxy-1-ethanol acetate of my invention by not covering or spoiling the organoleptic properties (aroma and/or taste) thereof; (ii) be non-reactive with the 1-n-butoxy-1-ethanol acetate of my invention and (iii) be capable of providing an environment in which the 1-n-butoxy-1-ethanol acetate can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of 1-n-butoxy-1-ethanol acetate employed in a particular instance can vary over a relatively wide range, depending upon the desired organoleptic effects to be achieved. Thus, correspondingly, greater amounts would be necessary in those instances wherein the ultimate food composition to be flavored (e.g., with a fresh, fruity, juicy, grape-like flavor) is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se or flavoring composition.

The use of insufficient quantities of 1-n-butoxy-1-ethanol acetate will, of course, substantially vitiate any possibility of obtaining the desired results while excess quantities prove needlessly costly and in extreme cases may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of 1-n-butoxy-1-ethanol acetate ranging from a small but effective amount, e.g., 0.05 parts per million, up to about 500 parts per million based on total composition, are suitable. Concentrations in excess of the maximum quantity stated are not normally recommended since they fail to provide commensurate enhancement of organoleptic properties. In those instances wherein the 1-n-butoxy-1-ethanol acetate is added to the foodstuff as an integral component of a flavoring composition, it is of course, essential that the total quantity of flavoring composition employed be sufficient to yield an effective 1-n-butoxy-1-ethanol acetate concentration in the foodstuff product.

Food flavoring compositions prepared in accordance with the present invention preferable contain the 1-n-butoxy-1-ethanol acetate in concentrations ranging from 0.025% up to about 15% by weight based on the total weight of the flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the 1-n-butoxy-1-ethanol acetate with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix, are obtained by mixing the dried solid components, e.g., starch, sugar and the like, and 1-n-butoxy-1-ethanol acetate in a dry blender until the requisite degree of uniformity is achieved.

It is presently preferred to combine with the 1-n-butoxy-1-ethanol acetate of my invention, the following adjuvants: Natural Orange Oil; Ethyl Acetate; Ethyl Butyrate, n-Propanol; Trans-2-hexenal; Oil of Cubeb; Phellandrene; beta-Phellandrene; Oil of Coriander; Oil of Pimento Leaf, Oil of Patchouli; Natural Lemon Oil; Acetaldehyde; Alpha-Terpineol; Citral; Carvone; Terpinolene; Alpha-Terpinene; Diphenyl; Alpha-Fenchyl Alcohol; Cineole; Limonene; Linalool; Geranyl Acetate; Noot-katone; Neryl Acetate; Heliotropin; Maltol; Vanillin; Ethyl Maltol; Ethyl Vanillin; Anisaldehyde; Alpha Pinene; Beta-Pinene; Beta-Caryophyllene; Dihydrocarveol; Piperonal; Piperine; Chavicine; Piperidine; Oil of Black Pepper, Black Pepper Oleo-resen; Capsicum; Oil of Nutmeg; Cardamom Oil; Clove Oil; Spearmint Oil; Oil of Peppermint; methyl anthranilate; ethyl acetate; ethyl anthranilate; ethyl butyrate; ethyl methyl phenyl glycidate; cinnamic alcohol; amyl valerianate; cinnamyl propionate; rhodinyl acetate; methyl beta-hydroxy butyrate; ethyl beta-hydroxy butyrate; 2-phenyl-3-carboethoxyfuran; bis(cyclohexyl) disulfide; amyl acetate; gamma decalactone; caprylic acid; n-hexyl acetate; coriander oil; n-hexyl isobutyrate; n-hexaldehyde; ethyl isovalerate; cis-3-hexenol; ethyl-2-methyl butyrate; trans-2-hexenol; apple fusel oil; maltol and $C_{10}$-Terpinyl Ethers as described in application for U.S. Patent, Ser. No. 872,937 filed on Jan. 27, 1978, now U.S. Pat. No. 4,131,687, issued on Dec. 26, 1978 (such as fenchyl ethyl ethers).

The 1-n-butoxy-1-ethanol acetate of my invention can be used to contribute fruity, floral, jasmine, pear-like, banana-like, grape-like and winey aromas to perfumes, perfumed articles and colognes. As olfactory agents, the 1-n-butoxy-1-ethanol acetate of my invention can be formulated into, or used as components of a "perfume composition" or can be used as components of a "perfumed article" (e.g., solid or liquid, anionic, cationic, nonionic or zwitterionic detergents, fabric softeners, fabric softener articles or hair conditioners, or the like) or the perfume composition may be added to perfume, perfumed articles or colognes.

The term "perfume composition" is used herein to mean a mixture of organic compounds, including, for example, alcohols, aldehydes, ketones, nitriles, ethers, lactones, acetals, hemiacetals, ester acetals, other than the 1-n-butoxy-1-ethanol acetate of my invention, natural essential oils, synthetic essential oils, and frequently, hydrocarbons, which are admixed so that the combined odors of the individual components produce a pleasant, or desired fragrance, e.g., a lemon fragrance. Such perfume compositions usually contain: (a) the main note or the "bouquet" or foundationstone of the composition; (b) modifiers which round-off and accompany the main note; (c) fixatives which include odorous substances, which lend a particular note to the perfume throughout all stages of evaporation, and substances which retard evaporation; and (d) top-notes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the 1-n-butoxy-1-ethanol acetate of this invention which will be effective in perfume compositions depends upon many factors, including the other ingredients, their amounts and the effects which are desired. It has been found that perfume composition containing as little as 0.5% of the 1-n-butoxy-1-ethanol acetate of this invention, or even less, can be used to impart an interesting fruity, floral, jasmine, pear-like, banana-like, grape-like and winey aroma to soaps, liquid and solid cationic, anionic, nonionic and zwitterionic detergents, cosmetics, powders, liquid and solid fabric softeners, dryer-added fabric softener articles, optical brightener compositions and other products. The amount employed can range up to 50% or higher and will depend on considerations of cost, nature of the end product, and the effect desired on the finished product and particular fragrance sought. Thus, in summary, the range of 1-n-butoxy-1-ethanol acetate in perfume compositions may range from 0.5% up to 50%.

The 1-n-butoxy-1-ethanol acetate of this invention can be used alone or in a perfume composition as an olfactory component in detergents and soaps, space odorants and deodorants; perfumes; colognes; toilet waters; bath salts; hair preparations such as lacquers, brilliantines, pomades and shampoos; cosmetic preparations such as creams, deodorants, hand lotions and sun screens; powders such as talcs, dusting powders, face powder and the like. When used as an olfactory component of a perfumed article, such as a solid or liquid anionic, cationic, nonionic or zwitterionic detergent, as little as 0.01% of the 1-n-butoxy-1-ethanol acetate will suffice to impart an interesting, fruity, floral, jasmine, pear-like, banana-like, grape-like, winey aroma. Generally no more than 1.0% is required. Thus, the range of 1-n-butoxy-1-ethanol acetate in perfumed articles will vary from 0.01% up to 1.0%.

In addition, the perfume composition containing the 1-n-butoxy-1-ethanol acetate of my invention can contain a vehicle or carrier for the 1-n-butoxy-1-ethanol acetate alone or with other ingredients. The vehicle can be a liquid such as an alcohol, such as ethanol, a glycol such as propylene glycol, or the like. The carrier can be an absorbent solid such as a gum or components for encapsulating the composition such as gelatin, which can be used to form a capsule wall surrounding the perfume oil as by means of coacervation.

An additional aspect of my invention provides an organoleptically improved smoking tobacco product and additives therefor including methods of making the same which overcome problems heretofore encountered in the creation or enhancement of specific desired sweet, fruity, winey, fresh berry-like notes. Such notes, both prior to and on smoking, in both the main stream and the side stream, may now be readily controlled and maintained at the desired uniform level regardless of variations in the tobacco components of the blend; or the nature of the filter used in conjunction with the smoking tobacco article.

This invention further provides improved tobacco additives and additives for materials used in the fabrication of tobacco articles (particularly smoking tobacco articles) and methods whereby desirable sweet, fruity, winey, fresh berry-like notes may be imparted to smoking tobacco products and may be readily varied and controlled to produce the desired uniform flavoring characteristics.

In carrying out this aspect of my invention, I add to smoking tobacco materials or a suitable substitute therefor (e.g., dried lettuce leaves) an aroma amd flavor additive containing as an active ingredient, 1-n-butoxy-1-ethanol acetate of my invention.

In addition to the 1-n-butoxy-1-ethanol acetate of my invention, other flavoring and aroma additives may be added to the smoking tobacco material or substitute therefor either separately or in admixture with 1-n-butoxy-1-ethanol acetate.

I. Synthetic Materials
Beta-methyl cinnamaldehyde;
Eugenol;
Dipentene;
Damascenone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexen-1-ol;
2-Methyl-5-isopropyl-1,3-nonadiene-8-one;
2-Methyl-5-isopropylacetophenone;
2-Hydroxy-2,5,5,8α-tetramethyl-1-(2-hydroxyethyl)-decahydronaphthalene;
Dodecahydro-3α,6,6,9α-tetramethylnaphtho(2,1-β-)furan;
4-hydroxyhexenoic acid, gamma-lactone;
Polyisoprenoid hydrocarbons defined in Example V of U.S. Pat. No. 3,589,372 issued on June 29, 1971

II. Natural Oils
Celery seed oil;
Coffee extract;
Bergamot oil;
Cocoa extract;
Nutmeg oil;
Origanum oil;

An aroma and flavoring concentrate containing the 1-n-butoxy-1-ethanol acetate of my invention and if, desired, one or more of the above-indicated additional flavoring additives may be added to the smoking tobacco material, to the filter or the leaf or paper wrapper or to a filter which is part of the smoking article. The smoking tobacco material may be shredded, cured, cased and blended tobacco material or tobacco substitutes (e.g., dried lettuce leaves) or mixtures thereof. The proportions of flavoring additives may be varied in accordance with taste, but insofar as enhancement of the imparting of sweet, fruity, winey, fresh-berry-like notes prior to and on smoking, in both the main stream and the side stream, I have found that satisfactory results are obtained if the proportion by weight of the sum total of 1-n-butoxy-1-ethanol acetate to smoking tobacco material is between 50 parts per million and 1500 parts per million (0.005%–0.15%) of the active ingredients to the smoking tobacco material. I have further found that satisfactory results are obtained if the proportions by weight of the sum total of 1-n-butoxy-1-ethanol acetate used to flavoring material is between 0.05:1 and 0.50:1.

Any convenient method for incorporating the 1-n-butoxy-1-ethanol acetate in the tobacco product may be employed. Thus, the 1-n-butoxy-1-ethanol acetate taken alone or together with other flavoring additives may be dissolved in a suitable solvent such as food grade ethanol, pentane, diethyl ether and/or other volatile organic solvents, and the resulting solution may either be sprayed on the cured, cased and blended tobacco material; or the tobacco or filter may be dipped into such solution. Under certain circumstances, a solution of the 1-n-butoxy-1-ethanol acetate taken alone or taken further together with other flavoring additives as set forth above, may be applied by means of a suitable applicator such as a brush or roller on the paper or leaf wrapper for the smoking tobacco product, or it may be applied to the filter by either spraying or dipping or coating.

Furthermore, it will be apparent that only a portion of the tobacco or substitute therefor need be treated, and the thus-treated tobacco may be blended with other tobacco before the ultimate tobacco product is formed. In such cases, the tobacco treated may have the 1-n-butoxy-1-ethanol acetate of my invention in excess of the amounts or concentrations above indicated so that when blended with other tobaccos, the final product will have the percentage within the indicated range.

While my invention is particularly useful in the manufacture of smoking tobacco such as cigarette tobacco, cigar tobacco and pipe tobacco, other tobacco products formed from sheeted tobacco dust or fines may also be used. As stated supra, the 1-n-butoxy-1-ethanol acetate of my invention can be incorporated with materials such as filter tip materials, seam paste, packaging materials and the like which are used along with the tobacco to form a product adapted for smoking. Furthermore, the 1-n-butoxy-1-ethanol acetate of my invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials or both.

It will thus be apparent that the 1-n-butoxy-1-ethanol acetate of my invention can be utilized to alter, modify, augment or enhance sensory properties, particularly organoleptic properties, such as flavor(s) and/or fragrance(s) of a wide variety of consumable materials.

The following examples serve to illustrate my invention, and this invention is to be considered restricted thereto only as indicated in the appended claims.

All parts and percentages given herein are by weight unless otherwise specified.

EXAMPLE I

PREPARATION OF 1-n-BUTOXY-1-ETHANOL ACETATE

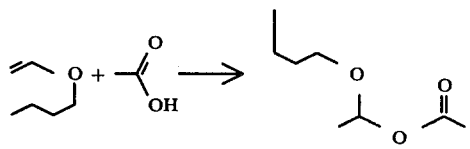

Into a 2000 ml reaction flask, equipped with stirrer, cooling bath, thermometer, addition funnel and nitrogen blanket apparatus, is added 420 ml of acetic acid (7.0 moles) and 3.0 ml of acetyl chloride. Dropwise over a period of 1.5 hours, while maintaining the reaction mass at 50°–72° C. is added 950 ml (7.7 moles) of n-butyl vinyl ether (770 grams). At the end of the addition of said n-butyl vinyl ether, the reaction mass is stirred for a period of six hours, while maintaining the temperature thereof at 30° C.

The reaction mass is then distilled through a 2" splash column yielding the following fractions:

| Fraction Number | Vapor Temp. °C. | Liquid Temp. °C. | Head Vac. mm. Hg. | Reflux Ratio R/D |
|---|---|---|---|---|
| 1 | 40/37 | 43/41 | 3/5 | RO |
| 2 | 37 | 42 | 3 | RO |
| 3 | 37 | 42 | 3 | RO |
| 4 | 45 | 50 | 5 | RO |
| 5 | 45 | 69 | 3 | RO |

FIG. 1 is the GLC profile for the 1-n-butoxy-1-ethanol acetate produced above.

Figure 2:
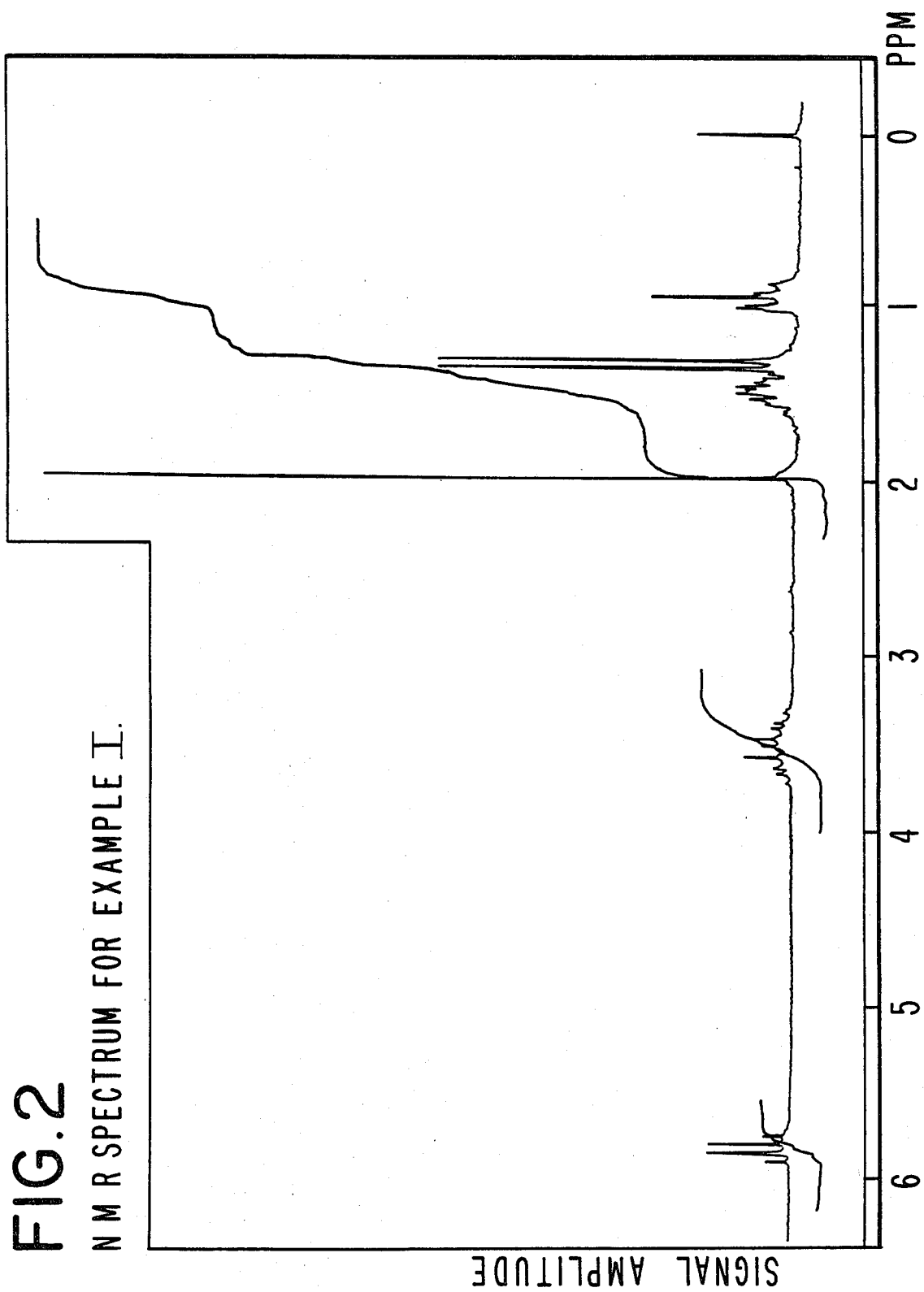
FIG. 2 is the NMR spectrum for 1-n-butoxy-1-ethanol acetate produced according to Example I.

FIG. 2 is the NMR spectrum for the 1-n-butoxy-1-ethanol acetate produced above.

Figure 3:
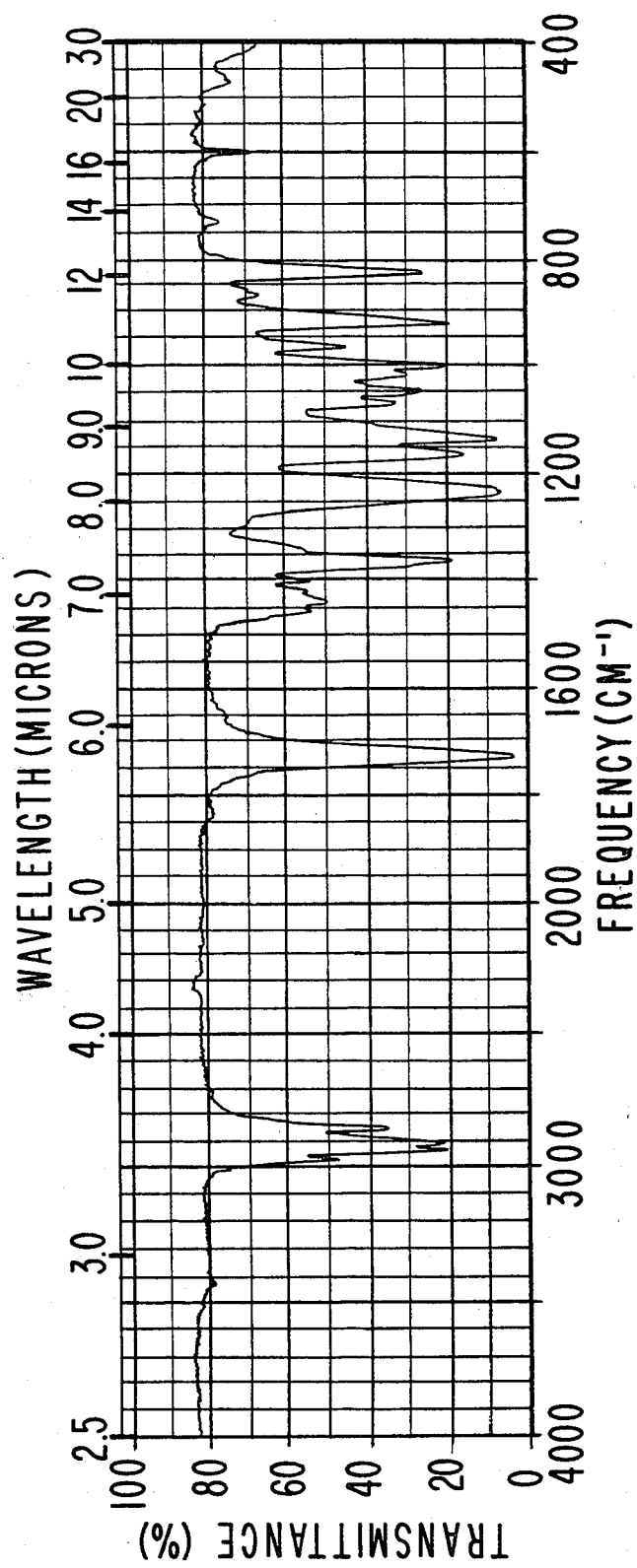
FIG. 3 is the infra-red spectrum for 1-n-butoxy-1-ethanol acetate produced according to Example I.

FIG. 3 is the infra-red spectrum for 1-n-butoxy-1-ethanol acetate produced above.

The NMR and the infra-red spectra, confirm that the structure of 1-n-butoxy-1-ethanol acetate is:

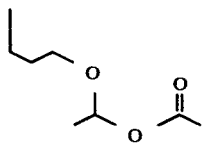

EXAMPLE IIA 500 mg. of beta-cyclic dextrin is dissolved in 40 ml. of water to which there is added a drop of 0.1 M sodium hydroxide solution to avoid having water with an acid pH. 1-n-butoxy-1-ethanol acetate prepared according to Example I in an amount of 0.3 ml, is then added to the solution. The container for the solution is immediately stoppered and shaken vigorously to obtain a homogeneous solution. Then another solution is prepared by dissolving 1.0 g of alpha-cyclic dextrin in 40 ml of water to which has been added, one drop of 0.1 M sodium hydroxide solution. 1-n-butoxy-1-ethanol acetate in an amount of 0.5 ml is then added to the resulting solution and the container is stoppered and shaken vigorously to obtain a homogeneous solution. Both solutions are then frozen and lyophilized overnight, to produce, respectively, beta-cyclic dextrin-1-n-butoxy-1-ethanol acetate and alpha-cyclic dextrin-1-n-butoxy-1-ethanol acetate complexes in dry form. These are analyzed colorimetrically using using 10 mg of each complex per 100 ml of water, and each complex is found to have bound 12% by weight of 1-n-butoxy-1-ethanol acetate. A second analysis using 30 mg of complex per 100 ml of water shows the beta-cyclic dextrin complex to have 10.8% by weight of 1-n-butoxy-1-ethanol acetate and the alpha-cyclic dextrin complex to have 11.4% of 1-n-butoxy-1-ethanol acetate. The colorimetric analysis is run in the following way: To 1 ml of aqueous sample solution containing 0.1 mg (or 0.01% by weight) of dissolved complex, there is added 1.0 ml of a saturated alcoholic solution of 2,4-dinitrophenylhydrazine and one drop of concentrated hydrochloric acid, the resulting solution is mixed, and then heated for 30 minutes at 50° C. After heating 10.0 ml of 10% potassium hydroxide in 70% alcohol is added, and the color is read at 480 millimicrons on a spectrophotometer. The concentration is read off a previously prepared color concentration curve. The foregoing assay is based on the method described by Snell, et al. in "Colorimetric Method of Analyses", vol. 3, page 253, D. Van Nostrand Co., Inc. New York 1953.

EXAMPLE IIB

About 2.5 mg of the beta-cyclic dextrin complex of Example IIA is added to 6.7 gm of a dry orange-flavored beverage mix comprising sucrose, citric acid and a cloud-forming agent. When the mix is dissolved in about 50 ml of water, the beverage has the characteristic odor and flavor of fresh oranges, and is judged to be superior in these respects over a beverage prepared in exactly the same way but in which the complex is omitted.

EXAMPLE III

ORANGE FLAVOR FORMULATION

An orange flavor formulation is prepared by admixing:

| Ingredients | Parts by Weight |
|---|---|
| Natural orange oil | 13.00 |
| 1-n-butoxy-1-ethanol acetate | 1.58 |
| Ethyl acetate | 0.10 |
| Ethyl butyrate | 0.50 |
| n-Propanol | 0.10 |
| trans-2-Hexenal | 0.10 |
| Ethyl Alcohol (95% food grade) | 60.00 |
| Fusel Oil | 0.05 |
| Propylene Glycol | 24.65 |

This flavor is denominated as Flavor "A". A second formulation Flavor "B" is prepared by adding 2-ethylidene-cis-3-hexenal (1% in food grade ethanol) to a portion of Flavor "A" in the ratio of 2 parts to 100 parts of Flavor "A". To a third formulation denominated as Flavor "C", the substance 1-n-butoxy-1-ethanol acetate, is substituted by acetaldehyde. To a fourth formulation denominated as "D", 1-n-butoxy-1-ethanol acetate is substituted with acetaldehyde and 2-ethylidene-cis-3-hexenal (1% in food grade ethanol) is added to it.

Each of Flavors "A", "B", "C" and "D" is added to the amount of 2 ounces per gallon of 32° Baume sugar syrup to produce a syrup for combination with water to form a drink. The beverage prepared using Flavors "A" and "B" are passable orange beverages of good character, flavor and intensity, whereas the flavors using "C" and "D" are not passable. The flavor prepared using "A" and "B" have a much improved flavor, particularly the flavor denominated as "B". The improvement contributed by the 1-n-butoxy-1-ethanol acetate (versus the acetaldehyde itself) is due to a much longer-lasting degree of freshness. The improvement contributed by the ethylidene hexanal is due to:

1. a greater degree of the natural character of freshly squeezed orange juice
2. an increase in the pulp-like notes
3. greater orange juice flavor depth.

The combination of 1-n-butoxy-1-ethanol acetate and the ethylidene hexenal gives rise to a highly unexpected, fresh, freshly squeezed, orange juice flavor.

EXAMPLE IV

APPLE FLAVOR FORMULATION

The following basic apple flavor formulation is prepared:

| Ingredients | Parts by Weight |
| --- | --- |
| Amyl acetate | 1.0 |
| Gamma decalactone | 1.5 |
| Caproic acid | 1.5 |
| n-Hexyl acetate | 2.5 |
| Coriander Oil | 0.5 |
| n-Hexyl iso-butyrate | 2.5 |
| n-Hexanal | 5.0 |
| Ethyl isovalerate | 5.0 |
| cis-3-Hexenol | 18.0 |
| Ethyl-2-methyl butyrate | 18.0 |
| trans-2-Hexenal | 18.0 |
| Apple Fusel Oil | 26.0 |
| Maltol | 0.5 |
| 95% food grade ethanol | 100.0 |

This basic apple flavor is compared, in water, with and without the addition of 1-n-butoxy-1-ethanol acetate at the rate of 20 ppm in water. The flavor with the addition of the 1-n-butoxy-1-ethanol acetate has a fresher and more juicy character than the flavor without the 1-n-butoxy-1-ethanol acetate. The flavor with the 1-n-butoxy-1-ethanol acetate is preferred unanimously by the panel.

In addition, 4 ppm acetaldehyde is then added to the basic apple flavor and compared with the flavor with the 1-n-butoxy-1-ethanol acetate. The flavor with the 1-n-butoxy-1-ethanol acetate gives freshness equal to that obtained using the acetaldehyde but gives a more interesting slight grape nuance (which can be described as a "white" grape-juice character.

Thus, the 1-n-butoxy-1-ethanol acetate produces not only the fresh character obtained when using acetaldehyde but also gives rise to the unexpected, unobvious and advantageous additional white grape-juice nuance not contained in the flavor which does not have the 1-n-butoxy-1-ethanol acetate added thereto.

EXAMPLE V

A. POWDER FLAVOR FORMULATION 20 g of the flavor formulation of Example IV is emulsified in a solution containing 300 g gum acacia and 700 g water. The emulsion is spray-dried with a Bowen Lab Model Drier utilizing 260 c.f.m. of air with an inlet temperature of 500° F., an outlet temperature of 200° F. and a wheel speed of 50,000 rpm.

B. SUSTAINED RELEASE FLAVOR

The following mixture is prepared:

| Ingredients | Parts by Weight |
| --- | --- |
| Liquid Apple Flavor of Example IV | 20 |
| Propylene Glycol | 9 |
| Cab-O-Sil ® M-5 Brand of Silica produced by the Cabot corporation of 125 High Street, Boston, Mass. 02110; Physical Properties: Surface Area: 200 m²/gm Nominal particle size: 0.012 microns Density: 2.3 lbs/cu. ft. | 5.00 |

The Cab-O-Sil is dispersed in the liquid apple flavor composition of Example IV with vigorous stirring, thereby resulting in a viscous liquid. 71 parts by weight of the powder flavor composition of Part 1, supra, is then blended into the said viscous liquid, with stirring at 25° C. for a period of 30 minutes, resulting in a dry, free flowing sustained release powder.

EXAMPLE VI 10 parts by weight of 50 Bloom pigskin gelatin is added to 90 parts by weight of water at a temperature of 150° F. The mixture is agitated until the gelatin is completely dissolved and the solution is cooled to 120° F. 20 parts by weight of the liquid apple flavor composition of Example IV is added to the solution which is then homogenized to form an emulsion having particle size typically in the range of 2–5 microns. This material is kept at 120° F. under which conditions, the gelatin will not jell.

Coacervation is induced by adding slowly and uniformly, 40 parts by weight of a 20% aqueous solution of sodium sulphate. During coacervation the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE VII

CHEWING GUM 100 parts by weight of chicle are mixed with 4 parts by weight of the flavor prepared in accordance with Example V. 300 Parts of sucrose and 100 parts of corn syrup are added. Mixing is effected in a ribbon blender with jacketed walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting apple flavor.

EXAMPLE VIII

CHEWING GUM

100 Parts by weight of chicle are mixed with 18 parts by weight of the flavor prepared in accordance with Example VI. 300 Parts of sucrose and 100 parts of corn syrup are then added. Mixing is effected in a ribbon blender with jacketed walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting apple flavor.

EXAMPLE IX

TOOTHPASTE FORMULATION

The following separate groups of ingredients are prepared:

| Parts by Weight | Ingredient |
|---|---|
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example V |
| 100.00 - TOTAL | |

PROCEDURE

1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste is formed
4. With stirring, the flavor of "D" is added and lastly the sodium-n-lauroyl sarcosinate
5. The resultant slurry is then blended for one hour. The completed paste is then transferred to a three roller mill and then homogenized, and finally tubed.

The resulting toothpaste, when used in a normal tooth-brushing procedure yields a pleasant apple flavor, of constant strong intensity throughout said procedure (1–1.5 minutes).

EXAMPLE X

CHEWABLE VITAMIN TABLETS

The flavor material produced according to the process of Example V is added to a Chewable Vitamin Tablet Formulation at a rate of 10 gm/Kg, which Chewable Vitamin Tablet Formulation is prepared as follows:

In a Hobart Mixer, the following materials are blended to homogeneity:

| Ingredients | Gms/1000 Tablets |
|---|---|
| Vitamin C (ascorbid acid) as ascorbic acid-sodium ascorbate mixture 1:1 | 70.11 |
| Vitamin B$_1$ (thiamine mononitrate) as Rocoat ® thiamine mononitrate 33⅓% (Hoffman La Roche) | 4.0 |
| Vitamin B$_2$ (riboflavin) as Rocoat ® riboflavin 33⅓% | 5.0 |
| Vitamin B$_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% | 6.6 |
| d-Biotin | 0.044 |
| Flavor of Example V | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong apple flavor for a period of 12 minutes.

EXAMPLE XI

CHEWING TABACCO

Onto 100 pounds of tobacco for chewing (85% Wisconsin leaf and 15% Pennsylvania leaf) the following casing is sprayed at the rate of 30%.

| Ingredients | Parts by Weight |
|---|---|
| Corn syrup | 60 |
| Licorice | 10 |
| Glycerine | 20 |
| Fig Juice | 4.6 |
| Prune Juice | 5 |
| 1-n-butoxy-1-ethanol acetate | 0.04 |

The resultant product is redried to a moisture content of 20%. On chewing, this tobacco has an excellent substantially consistent, long-lasting fruity taste with apple, grape and winey characteristics in conjunction with the tobacco notes.

EXAMPLE XII

A tobacco blend is made up by mixing the following materials:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model filter cigarettes are treated in the tobacco section with 1-n-butoxy-1-ethanol acetate produced according to Example I at 100 ppm per cigarette. Another one-third of these model cigarettes is treated in the filter with 1-n-butoxy-1-ethanol acetate produced according to Example I, at the rate of $2 \times 10^{-5}$ gm. When evaluated by paired comparison, the cigarettes treated both in the tobacco and in the filter with the 1-n-butoxy-1-ethanol acetate are found, in smoke flavor, to be more tobacco-like, when enhanced sweet, fruity, winey and fresh berry nuances. When replacing 1-n-butoxy-1-ethanol acetate with acetaldehyde, the flavor is much weaker, and the amount of freshness and "lift" to the smoke is much less. 1-n-butoxy-1-ethanol acetate gives an intense, freshness and lift to smoke, when compared to cigarettes either without anything added, or with acetaldehyde added in the same ratio.

EXAMPLE XIII

The following perfume formulation is prepared:

| Ingredients | Parts by Weight |
| --- | --- |
| Geranium bourbon | 175 |
| Citronellol | 150 |
| Geraniol | 100 |
| Phenyl ethyl alcohol | 90 |
| Amyl cinnamic aldehyde | 200 |
| Cyclamal | 20 |
| Lyral[1] | 100 |
| Tetrahydro linalool | 37.5 |
| Citronellyl acetate | 125 |
| Phenyl ethyl acetate | 5 |
| Phenyl acetaldehyde dimethyl acetal | 10 |
| Cinnamic alcohol | 35 |
| Terpineol | 100 |
| Linalyl acetate | 25 |
| Musk ketone | 10 |
| Indole | 10 |
| Geranyl nitrile | 10 |
| 7-methyl-3-methylene-6-octenenitrile | 10 |
| 1-ethoxy-1-ethanol acetate | 25 |

[1]Lyral is the registered trademark of International Flavors & Fragrances Inc., for 4-(4-methyl, 4-hydroxyamyl)-$\Delta^3$-cyclohexene carboxaldehyde.

The addition of 1-n-butoxy-1-ethanol acetate to the foregoing formulation, which is a lemon fragrance, imparts a freshness to the lemon fragrance, causing it to be more natural-like in aroma, and in addition, causing it to be longer-lasting in aroma and in intensity.

EXAMPLE XIV

PREPARATION OF A COSMETIC POWDER COMPOSITION

A cosmetic powder is prepared by mixing in a ball mill, 100 g of talcum powder with 0.25 g of the perfume composition prepared according to Example XIII. It has an excellent, fresh, lemony aroma. The "fresh" aroma nuance is imparted to this cosmetic powder, as a result of the use of 1-n-butoxy-1-ethanol acetate.

EXAMPLE XV

PERFUMED LIQUID DETERGENT

Concentrated liquid detergent (Lysine salt of n-dodecylbenzene sulfonic acid, as more specifically described in U.S. Pat. No. 3,948,818 issued on Apr. 6, 1976) with fresh, lemony aroma nuances are prepared containing 0.10%, 0.15% and 0.20% of the fragrance prepared according to Example XIII. They are prepared by adding and homogeneously mixing the appropriate quantity of fragrance formulation prepared according to Example XIII in the liquid detergent. The detergents all possess excellent, fresh lemony aroma, the intensity increasing with greater concentrations of perfume composition of Example XIII. This "fresh" aroma is contributed by the 1-n-butoxy-1-ethanol acetate produced according to Example I.

EXAMPLE XVI

PREPARATION OF A COLOGNE AND HANDKERCHIEF PERFUME

The composition prepared according to Example XIII, is incorporated into a cologne at concentrations of 2.0%, 2.5%, 3.0%, 3.5%, 4.0%, 4.5% and 5.0% in 85%, 90% and 95% aqueous food grade ethanol solutions, and into handkerchief perfume at concentrations of 15%, 20%, 25% and 30% (in 85%, 90% and 95% aqueous food grade ethanol solutions). Distinctive and definitive fresh lemony aromas are imparted to the cologne and to the handkerchief perfume at all levels indicated above. The "fresh" aroma nuance is contributed by the 1-n-butoxy-1-ethanol acetate produced according to Example I.

EXAMPLE XVII

PREPARATION OF SOAP COMPOSITION

One hundred grams of soap chips (IVORY ®, registered trademark of the Procter & Gamble Co. of Cinncinati, Ohio) are mixed with one gram of the formulation of Example XIII, until a homogeneous composition is obtained. The homogeneous composition is then treated under three atmospheres pressure at 180° C. for a period of three hours and the resulting liquid is placed into a soap mold. The resulting soap cake, on cooling, manifests an excellent, fresh lemony aroma, with the "fresh" nuance being contributed by the 1-n-butoxy-1-ethanol acetate produced according to Example I.

EXAMPLE XVIII

PREPARATION OF A SOLID DETERGENT COMPOSITION

A detergent is prepared from the following ingredients according to Example I of Canadian Pat. No. 1,007,948:

| Ingredients | Percent by Weight |
| --- | --- |
| "Neodol 45-II" (a $C_{14}$–$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed with 0.15 grams of the perfume formulation of Example XIII. The detergent sample has an excellent, fresh lemony aroma. The "fresh" nuance is imparted as a result of the use of 1-n-butoxy-1-ethanol acetate produced according to Example I.

EXAMPLE XIX

Utilizing the procedure of Example I of column 15 of U.S. Pat. No. 3,632,396, a nonwoven cloth substrate useful as a dryer-added fabric softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):

57 percent $C_{20-22}$ HAPS
22 percent isopropyl alcohol
20 percent antistatic agent
1 percent of the perfume composition of Example XIII (which gives rise to a fresh lemony aroma) (the fresh nuance is contributed by the 1-n-butoxy-1-ethanol acetate produced according to Example I)

A fabric softening composition prepared as set forth above having the above aroma characteristics, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth above is imparted in a pleasant manner to the headspace in the dryer on operation thereof, using said dryer-added, fabric softening non-woven fabric.

The disclosure of U.S. Pat. No. 3,632,396 in its entirety is hereby incorporated into the instant patent application. Thus, the fabric softening articles as covered by U.S. Pat. No. 3,632,396 can all be incorporated with the 1-n-butoxy-1-ethanol acetate produced according to Example I herein and can also be incorporated with 1-ethoxy-1-ethanol acetate of Example I of parent application for U.S. Letters Patent Ser. No. 176,111 filed on Aug. 7, 1980 giving rise to aroma effects as set forth above in Example XIX.

EXAMPLE XX

The following mixture is prepared:

| Ingredients | Parts by Weight |
|---|---|
| Methyl anthranilate | 11.0 |
| Ethyl acetate | 9.0 |
| Ethyl anthranilate | 2.5 |
| Ethyl butyrate | 2.0 |
| Ethyl methyl phenyl glycidate | 1.5 |
| Cinnamic alcohol | .3 |
| Cognac oil | .1 |
| Ethyl alcohol | 73.6 |

The above mixture is judged to be an acceptable grape flavor when evaluated in a sweetened and acidified aqueous tasting solution. 2.0 parts by weight of 1-n-butoxy-1-ethanol acetate produced according to Example I is added to the above flavor and a significant improvement in aroma and taste is noted. It is judged to be a better blended, more natural flavor and reminiscent of natural concord grape but also containing "winey" notes. It is a more rounded and has more grape fidelity imparting the nuance of wine with a certain mustiness.

When, in addition, 1.5 parts by weight of 2-phenyl-3-carboethoxyfuran and 0.09 parts of bis(cyclohexyl)disulfide (as indicated in U.S. Pat. No. 3,917,870 at Example XXV) is added, even more "wineyness" with a "vermouth-like" character is imparted to this flavor.

EXAMPLE XXI

GRAPE JUICE

The following grape flavor formulation is prepared:

| Ingredients | Parts by Weight |
|---|---|
| Methyl anthranilate | 11.0 |
| Ethyl acetate | 9.0 |
| Ethyl anthranilate | 2.5 |
| Ethyl butyrate | 2.0 |
| Ethyl methyl phenyl glycidate | 1.5 |
| Cinnamic alcohol | .3 |
| Cognac oil | .1 |
| Ethyl alcohol | 73.6 |
| 2-phenyl-3-carboethoxyfuran | 1.5 |
| bis(cyclohexyl)disulfide | 1.5 |
| 1-n-butoxy-1-ethanol acetate produced according to Example I | 1.0 |

A grape juice concentrate is prepared from natural grape juice by vacuum evaporation process. A concentration of 46° Brix is obtained which is combined with 100-fold natural grape essence in the ratio of 100:1. To this is added sufficient flavor as set forth above to provide a level of 100 ppm in the reconstituted grape juice prepared from the concentrate. The reconstituted grape juice produced using the above formulation is compared with natural grape juice and the reconstituted grape juice is found by a bench panel to be even more preferable than the natural grape juice particularly in its natural winey and fresh grape and "white" grape characteristics by a bench panel of three members.

What is claimed is:

1. A toothpaste comprising an aroma or taste modifying, augmenting or enhancing quantity of 1-n-butoxy-1-ethanol acetate having the structure:

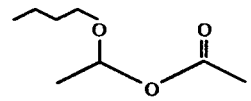

and in intimate admixture therewith, a toothpaste base.

2. A process for augmenting or enhancing the taste of a toothpaste comprising the step of adding to a toothpaste base, a taste modifying, augmenting or enhancing quantity of 1-n-butoxy-1-ethanol acetate having the structure:

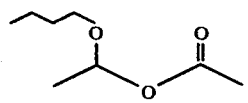

* * * * *